United States Patent
Fisher et al.

(10) Patent No.: US 10,994,451 B2
(45) Date of Patent: May 4, 2021

(54) METHOD FOR ENHANCING ULTRASOUND VISIBILITY OF HYPERECHOIC MATERIALS

(71) Applicant: Devicor Medical Products, Inc., Cincinnati, OH (US)

(72) Inventors: John S. Fisher, Belleair, FL (US); Frederick Ahari, Belleair Beach, FL (US)

(73) Assignee: Devicor Medical Products, Inc., Cincinnati, OH (US)

( * ) Notice: Subject to any disclaimer, the term of this patent is extended or adjusted under 35 U.S.C. 154(b) by 137 days.

(21) Appl. No.: 16/279,265

(22) Filed: Feb. 19, 2019

(65) Prior Publication Data

US 2019/0176372 A1   Jun. 13, 2019

Related U.S. Application Data

(63) Continuation of application No. 12/022,531, filed on Jan. 30, 2008, now abandoned.

(51) Int. Cl.
*B29C 39/10* (2006.01)
*A61B 90/00* (2016.01)
*A61B 17/00* (2006.01)

(52) U.S. Cl.
CPC .............. *B29C 39/10* (2013.01); *A61B 90/39* (2016.02); *A61B 2017/00004* (2013.01); *A61B 2017/00526* (2013.01); *A61B 2017/00898* (2013.01); *A61B 2090/3925* (2016.02)

(58) Field of Classification Search
None
See application file for complete search history.

(56) References Cited

U.S. PATENT DOCUMENTS

| | | |
|---|---|---|
| 3,855,382 A | 12/1974 | Takeya |
| 4,774,957 A | 10/1988 | Nambu et al. |
| 5,423,736 A | 6/1995 | Cartmell et al. |
| 5,489,437 A | 2/1996 | Marra |
| 5,526,822 A | 6/1996 | Burbank et al. |
| 5,578,661 A | 11/1996 | Fox et al. |
| 5,873,827 A | 2/1999 | Russell |

(Continued)

FOREIGN PATENT DOCUMENTS

WO  WO 2000/045854 A2  8/2000

OTHER PUBLICATIONS

Di Benedetto, F., et al. "Patterning polyacrylamide hydrogels by soft lithography." Nanotechnology 16.5 (2005) S165.

(Continued)

*Primary Examiner* — Katherine L Fernandez
(74) *Attorney, Agent, or Firm* — Frost Brown Todd LLC

(57) ABSTRACT

A permanent or temporary marker is embedded within a hydrogel plug used in a biopsy procedure to indicate the location of a suspicious lesion so that the marker may be found in a subsequent surgical procedure. A combination of at least one permanent and at least one temporary marker may be used. Inserts of differing sizes and shapes may also be placed into the hydrogel plugs during their manufacturing process and removed from the plugs after the plugs have cured so that air-filled cavities are left in the plug. These cavities are temporary but may be used to augment location of a permanent marker.

21 Claims, 2 Drawing Sheets

(56) References Cited

U.S. PATENT DOCUMENTS

| | | | |
|---|---|---|---|
| 5,882,557 A | 3/1999 | Hayakawa et al. | |
| 5,928,164 A | 7/1999 | Burbank et al. | |
| 6,017,316 A | 1/2000 | Ritchart et al. | |
| 6,086,544 A | 4/2000 | Hibner et al. | |
| 6,106,473 A | 8/2000 | Violante et al. | |
| 6,162,187 A | 12/2000 | Buzzard et al. | |
| 6,312,457 B1 | 11/2001 | DiMatteo et al. | |
| 6,372,248 B1 | 4/2002 | Qin et al. | |
| 6,432,065 B1 | 8/2002 | Burdorff et al. | |
| 6,544,185 B2 | 4/2003 | Montegrande | |
| 6,626,849 B2 | 9/2003 | Huitema et al. | |
| 6,723,781 B1 | 4/2004 | Frate et al. | |
| 6,725,083 B1* | 4/2004 | Burbank | A61K 49/006 600/414 |
| 6,752,768 B2 | 6/2004 | Burdorff et al. | |
| 7,329,414 B2 | 2/2008 | Fisher et al. | |
| 7,442,171 B2 | 10/2008 | Stephens et al. | |
| 7,556,602 B2 | 7/2009 | Wang et al. | |
| 7,648,466 B2 | 1/2010 | Stephens et al. | |
| 7,790,141 B2* | 9/2010 | Pathak | A61P 3/00 424/1.89 |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 8,083,687 B2 | 12/2011 | Parihar | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,280,486 B2 | 10/2012 | Miller et al. | |
| 8,454,531 B2 | 6/2013 | Speeg et al. | |
| 8,622,924 B2 | 1/2014 | Speeg et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,649,175 B2 | 5/2017 | Ahari et al. | |
| 2003/0165569 A1 | 9/2003 | Levy et al. | |
| 2004/0030262 A1 | 2/2004 | Fisher et al. | |
| 2004/0042582 A1 | 3/2004 | Ein-Gal | |
| 2005/0143656 A1* | 6/2005 | Burbank | A61M 37/0069 600/458 |
| 2005/0148995 A1 | 7/2005 | Shepard et al. | |
| 2005/0234336 A1 | 10/2005 | Beckman et al. | |
| 2005/0240098 A1 | 10/2005 | Zhong et al. | |
| 2006/0074345 A1 | 4/2006 | Hibner | |
| 2006/0193892 A1 | 8/2006 | Furst et al. | |
| 2006/0293581 A1 | 12/2006 | Plewes et al. | |
| 2007/0239016 A1 | 10/2007 | Fisher | |
| 2008/0208347 A1 | 8/2008 | Muratoglu et al. | |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2013/0324882 A1 | 12/2013 | Mescher | |

OTHER PUBLICATIONS

Brahim, Sean, Dyer Narinesingh, and Anthony Guiseppi-Elie. "Synthesis and hydration properties of pH-sensitive p (HEMA)-based hydrogels containing 3-(trimethoxysilyl) propyl methacrylate." Biomacromolecules 4.3 (2003): 497-503.
European Examination Report dated May 22, 2015 for Application No. EP 08872137.8, 5 pages.
International Search Report and Written Opinion dated Jul. 22, 2009 for International Application No. PCT/US2008/086376, 5 pages.
U.S. Appl. No. 12/022,531; and.
U.S. Appl. No. 15/261,607.

* cited by examiner

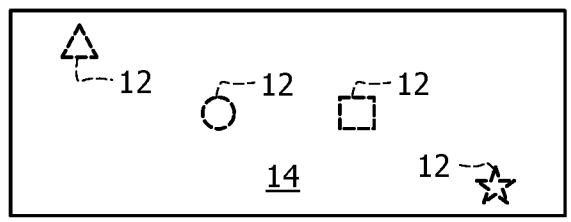
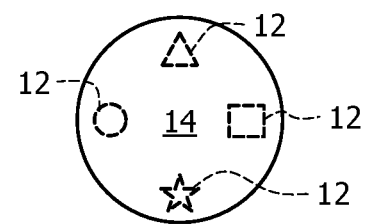
FIG. 1A  FIG. 1B
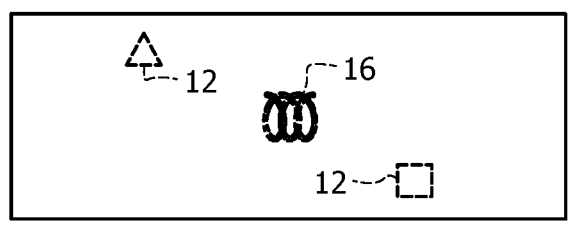
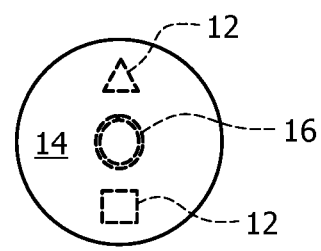
FIG. 2A  FIG. 2B
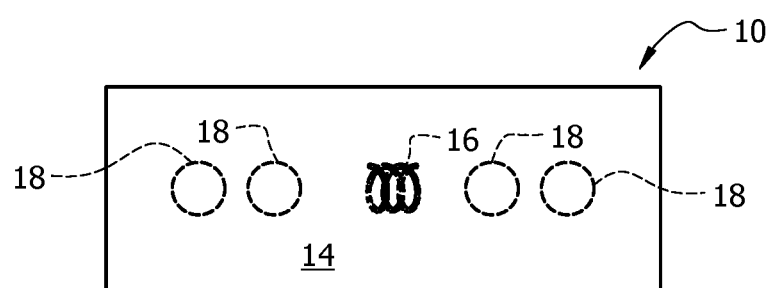
FIG. 3

METHOD FOR ENHANCING ULTRASOUND VISIBILITY OF HYPERECHOIC MATERIALS

CROSS-REFERENCE TO RELATED DISCLOSURES

This application is a continuation of U.S. application Ser. No. 12/022,531, filed Jan. 30, 2008, entitled "Method of Enhancing Ultrasound Visibility of Hyperechoic Materials," now published as U.S. Publication No. 2009/0088635 on Apr. 2, 2009, the disclosure of which is hereby incorporated by reference herein.

BACKGROUND OF THE INVENTION

1. Field of the Invention

This invention relates, generally, to a method for improving the visibility of a hyperechoic marker or markers under ultrasound. Such markers are used to indicate the location of a tumor or lesion so that a procedure to remove such lesion or tumor may be performed weeks or months after the marker has been implanted. More particularly, it relates to markers that incorporate hydrogels to enhance the visibility of the markers with imaging techniques such as ultrasound and to methods for making such markers.

2. Description of the Prior Art

A permanent metal or hard plastic, such as a permanent, bio-compatible plastic such as polyethylene, or temporary, bioabsorbable, biocompatible plastic such as PGA/PLA, or other suitable marker must be left at a biopsy site at the completion of a biopsy if the site is to be located again in the future. Biodegradable markers are not permanent and therefore cannot be relied upon if a biopsy site is to be relocated at a time remote from the time of the biopsy. However, there are applications where a temporary, biodegradable marker may have utility, either when used alone, in combination with other temporary markers, or in combination with one or more permanent markers. Suture and collagen-based markers are not suitable as markers because they are hyperechoic, i.e., difficult to see under ultrasound because such materials are easily confused with other shadowing normal structures in the body such as fibrous tissue, fatty tissue, ducts in breast tissue, and the like, for example. Such tissue provides a background clutter that masks the presence of a marker made of metal, hard plastic, or other hyperechoic material.

Water, unlike metal, hard plastic, and other hyperechoic materials, is hypoechoic, i.e., easy to see under imaging techniques such as ultrasound. Therefore it would be advantageous if a marker made of a hyperechoic material such as metal or hard plastic could be surrounded by an easily seen quantity of water.

However, the art includes no means for surrounding a hyperechoic marker with water at a biopsy site.

There is a need, then, for a permanent marker that is surrounded by water after it has been positioned at a biopsy site.

There is also a need, however, for a non-permanent, i.e., temporary marker that is surrounded by a hypoechoic material such as water at a biopsy site.

Moreover, there is a need for both permanent and temporary markers formed of hyperechoic materials, or temporary hyperechoic markers alone, surrounded by a hypoechoic material.

A need also exists for a hydrogel manufacturing process that produces a cured and dehydrated plug or marker that contracts in length and increases in diameter upon being hydrated.

There is also a need for a hydrogel manufacturing process that produces a cured and dehydrated plug or marker that contracts in width and increases in length and height upon being hydrated.

There is also a further need for a hydrogel manufacturing process that produces a cured and dehydrated plug or marker that contracts radially and increases in length upon being hydrated.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for a dehydrated marker that encapsulates a permanent hyperechoic marker, a temporary hyperechoic marker, or permanent and temporary hyperechoic markers in combination with one another, and that facilitates imaging of said hyperechoic markers is met by this new, useful, and non-obvious invention.

The long-standing but heretofore unfulfilled need for a dehydrated marker that contracts in length and increases in diameter, contracts in width and increases in length, or radially contracts and increases in length when hydrated, and a method for making such a marker, is also met by this invention.

Hydrogel, in order to be effective in the application of this invention, should contain about eighty to ninety percent (80%-90%) water. Hydrogels can contain higher or lower percentages of water but the range of eighty to ninety percent is believed to be optimal for the purposes of this invention but this invention is not limited to that particular range. Forming a biopsy marker from a hydrogel therefore provides a way to contain water so that it does not flow. It would be advantageous to embed a permanent hyperechoic marker within a cured and dehydrated hydrogel marker or plug. It would also be advantageous to embed a temporary hyperechoic marker, or a combination of permanent and temporary hyperechoic markers within a cured and dehydrated marker or plug. The plug would become hydrated by natural body moisture after being positioned at a biopsy site, thereby surrounding the permanent marker with water. The water would be easily seen under ultrasound and therefore the marker it surrounds would be easy to see.

The permanent marker may be positioned in the center of the hydrogel or off-center with respect thereto. A temporary marker, or a combination of permanent and temporary markers, may also be so positioned. The markers may even be positioned external to the hydrogel. In the latter case, a record may be made to the effect that the marker or markers will be found at the six o'clock position relative to the hydrogel, or the like.

The novel hydrogel polymer has a permanent or temporary marker, or a combination of permanent and temporary markers formed of metal, hard plastic, or other hyperechoic material embedded within the polymer. The hydration of the polymer by the natural moisture of the tissue surrounding it causes expansion of the polymer and thus minimizes the risk of migration. The growing hydrogel centers itself in the biopsy cavity as it grows.

The novel hydrogel composition does not include PGA/PLA. It is preferably peg-based and has advantages in imaging. Specifically, the plug is mostly water when hydrated. This provides a significant advantage because water is easily visible when ultrasound is employed as aforesaid.

The novel marker has two (2) imaging stages. The plug is solid and dry when it is deployed initially to mark the cavity created by a biopsy procedure.

The solid, dry plug is seen as a shadowing, hyperechoic, linear object with posterior acoustic shadowing on ultrasound.

However, as the hydrogel expands, due to naturally-present moisture from the surrounding tissue, the hydration enables increasing sound through transmission, appears more and more hypoechoic, and is easy to visualize on follow up ultrasound studies. The hydrogel, when hydrated, appears black in color, centers itself in the biopsy or other cavity as it grows, and frames the permanent, temporary, or combination of permanent and temporary markers.

The polymer plug is molded and cured into different shapes to avoid confusion with normal breast structures such as ducts. The shapes can be rod-like, spiral, round, toroidal, rectangular, string of pearls or any other predetermined geometrical configuration that does not have an appearance that resembles a naturally-occurring feature.

The hypoechoic nature of the hydrated plug enables ultrasound visibility of the permanent, temporary or combination of permanent and temporary markers within the hydrogel hydrated plug because the permanent, temporary, or permanent/temporary combination marker is outlined as a specular reflector within a hypoechoic hydrated marker plug having a water-like nonreflective substrate.

Water is the most easily visualized substrate under ultrasound. The permanent, temporary, or combination of permanent and temporary markers of this invention can have any shape that are not easily confused with a natural shape as mentioned above and it can be made of any permanent metallic-like or hard plastic material. Helical shapes having a hollow interior is a preferred shape because it allows the polymer to better retain the marker within.

Permanent and temporary markers may also be augmented by cavities formed in the hypoechoic material that encapsulates the markers. Such cavities are hypoechoic and thus serve to further indicate the location of the marker. The size and shape of the cavity or cavities is determined at the time the plug is manufactured. Specifically, the cavity or cavities are formed by inserts of differing shapes and sizes that are positioned inside the hydrogel during the curing process. The inserts are removed from the hydrogel after the hydrogel has cured, leaving the cavity or cavities in the hydrogel. The cavities are air-filled and thus reflect under ultrasound imaging in a way that differs from the reflection of the hydrogel. The cavities are not permanent because the air gradually escapes. The length of time required for the air to escape depends upon the size of the cavity, the shape of the cavity and whether or not the cavity is completely encapsulated or is in communication with the surface of the hydrogel.

An elongate suture may also have a first end embedded in a hydrogel plug during the curing and hydration process so that a second end of the suture may be positioned externally of a patient's body after a biopsy procedure.

The permanent, temporary, or combination permanent and temporary metallic or hard plastic markers may have a rod shape, a cylindrical shape, a coil shape, or other suitable shape. The coil configuration allows hydrogel to cure inside the core of the coil and between the loops of the coil to achieve a complete and smooth coverage of the hyperechoic marker by the hypoechoic hydrogel.

The novel marker or markers have several medical applications for soft tissue implants with a controlled RE/LC ratio. For example, it may be used as a soft tissue or void filler in cosmetic applications. A physician would start with a small size implant that expands in time to fill a cavity in a radial direction only without any longitudinal expansion.

Hydrogel implants post hydration are softer than most conventional implants and can take different shapes in filling soft tissue cavities. Expansion in the length direction may need to be controlled to maintain the desired shape.

There are also applications that require a higher than usual expansion rate, and there are applications where higher expansion rates are needed for small dehydrated implants in one direction only while contraction or shrinkage occurs in a different direction.

A primary advantage of the novel markers is that they provide a metal, hard plastic, or other permanent, temporary or combination marker that is easy to see under imaging because it is surrounded by water due to the hydration of the hydrogel within which it is embedded.

These and other advantages will become apparent as this disclosure proceeds. The invention includes the features of construction, arrangement of parts, and combination of elements set forth herein, and the scope of the invention is set forth in the claims appended hereto.

BRIEF DESCRIPTION OF THE DRAWINGS

For a fuller understanding of the nature and objects of the invention, reference should be made to the following detailed description, taken in connection with the accompanying drawings, in which:

FIG. 1A is a front elevational view of a first embodiment of a hydrogel plug in a position of repose having a plurality of temporary, biodegradable markers embedded therewithin;

FIG. 1B is an end elevational view of the embodiment depicted in FIG. 1A;

FIG. 2A is a front elevational view of a second embodiment of a hydrogel plug in repose having a combination of temporary and permanent markers;

FIG. 2B is an end elevational view of the embodiment depicted in FIG. 2A;

FIG. 3 is a front elevational view of a hydrogel plug having a plurality of large, round cavities formed therein;

DETAILED DESCRIPTION OF THE PREFERRED EMBODIMENT

Figure 4:
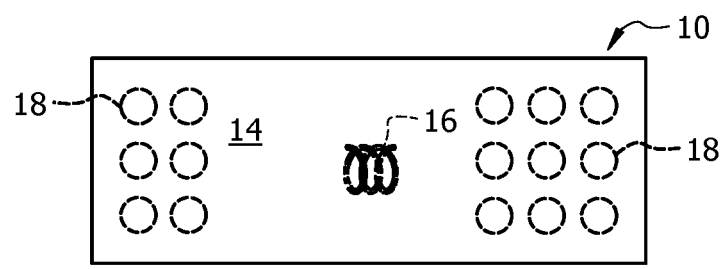
FIG. 4 is a front elevational view of a hydrogel plug having a plurality of small, round cavities formed therein.

Referring now to FIGS. 1A and 1B, it will there be seen that a first illustrative embodiment of the invention is denoted as a whole by the reference numeral 10.

Hydrogel plug 10 includes a plurality of temporary markers, collectively denoted 12, embedded within a hydrogel material 14 having, in this first embodiment, a shape designed to inhibit migration of the plug within tissue. The FIG. 1A configuration is the "in repose" configuration of plug 10. Markers 12 may be formed of metal, hard plastic, or other permanent material but the depicted markers 12 are formed of a temporary, biodegradable materials.

FIGS. 1A and 1B depict multiple temporary markers 12 of differing sizes and shapes just to illustrate that the markers may be provided in an infinite variety of geometrical configurations. Thus it should be understood that a single temporary marker 12 is within the scope of this invention. Accordingly, the novel method of this invention includes the step of selecting at least one temporary, biodegradable marker from a group of markers that includes permanent and temporary, biodegradable markers.

The preferred temporary, biodegradable marker is a biodegradable molded polymer made of PGA/PLA or other suitable biodegradable materials that are compatible and otherwise suitable for use in human tissue.

In the alternative, as depicted in FIGS. 2A and 2B, one or more permanent markers 16 may be used in combination with one or more temporary markers 12. It should be noted that the marker or markers may be embedded in the center of the hydrogel 14 or at any off center location. It may even be positioned outside the hydrogel if a record is made recording the location of the marker relative to the hydrogel.

The embodiment of FIG. 3 includes a permanent marker and plurality of large, round air-filled cavities, collectively denoted 18. These air-filled cavities reflect ultrasound in a way that is distinguishable from hydrogel reflection and thus said cavities serve to help point out the location of the permanent marker. The cavities may also be provided in hydrogel plugs having no permanent marker or markers embedded therein. One or more of the cavities could also be in open communication with the surface of the hydrogel plug. Moreover, the cavities need not have a common size or shape and they may be of any size and any predetermined geometrical configuration. The use of a single cavity is also within the scope of this invention.

FIG. 4 provides an example where the cavities 18 are smaller in size and greater in number than the embodiment of FIG. 3.

Figure 5:
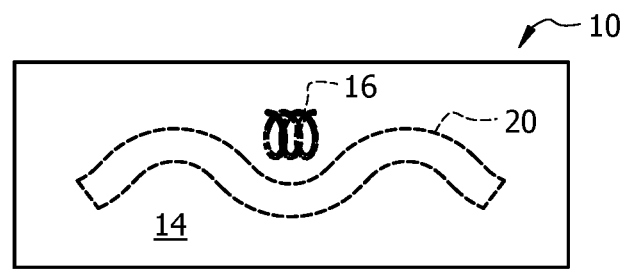
FIG. 5 is a front elevational view of a hydrogel plug having a completely encapsulated sinusoidal cavity formed therein.
Figure 6:
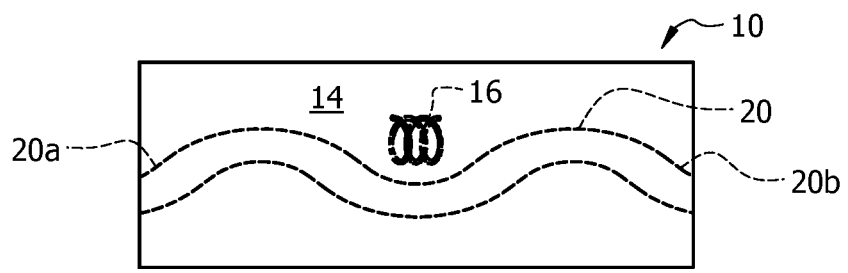
FIG. 6 is a view like that of FIG. 5 but where the opposite ends of the sinusoidal cavity are in open communication with a surfaced of the hydrogel plug.

The embodiment of FIG. 5 includes a fully embedded sinusoidal cavity 20 and the embodiment of FIG. 6 includes a sinusoidal cavity that is in open communication with the surface of the hydrogel plug at its opposite ends 20a, 20b. Another drawing could be provided to depict only one end of the sinusoidal cavity in such open communication and still further drawings could depict a maximum or minimum amplitude of cavity 20 in such open communication, but such drawings are not provided to conserve resources.

Figure 7:
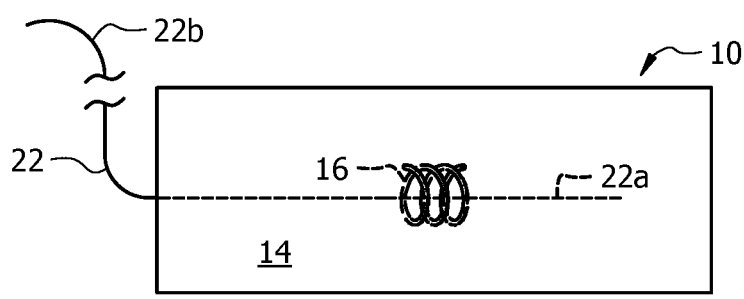
FIG. 7 is a front elevational view of a hydrogel plug having a first end of an elongate suture embedded therein so that a second end of said suture may be positioned externally of the patient when the biopsy procedure is completed.

The embodiment of FIG. 7 depicts elongate suture 22 having a first end 22a embedded in a hydrogel plug so that second end 22b thereof may be positioned externally of a patient's body after a biopsy procedure has been completed.

This invention is not limited to any particular shape. Hydrogel material 14 may be formed into any shape that inhibits migration.

Marker 12 could also be positioned in the interior of a balloon or other bladder and said balloon or bladder could be filled with water. Although this may not be a practical way of identifying the location of a permanent or temporary marker, or combination thereof, it would work because water is hypoechoic and such an apparatus would therefore identify the location of a hyperechoic marker.

The applications of this invention are not limited to permanent, temporary or combination markers encapsulated in hydrogel for use in biopsy procedures. The same method may be used to facilitate detection of any metal, hard plastic, or other hyperechoic structures in the body such as vascular stents, surgical staples, embolization coils, radiation seed, aneuryism clips, electrode stimulation wires, prosthetic valves, stent grafts, biliary stents, drug delivery metal containers or dispensers, and the like.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method for facilitating ultrasound viewing of a hydrogel marker when the hydrogel marker is disposed within tissue, comprising:

forming a body of the hydrogel marker, the body comprising a hydrogel material;

placing a plurality of internal structures within the hydrogel material; and maintaining the plurality of internal structures during a curing process of the hydrogel material to form a plurality of air filled cavities within the cured hydrogel material, wherein the air filled cavities reflect under ultrasound imaging in a way that differs from a reflection of the hydrogel material, wherein after the curing process, the hydrogel marker comprises the hydrogel material cured in the curing process and having the plurality of air filled cavities to facilitate ultrasound location of the hydrogel marker when the hydrogel marker is disposed within tissue.

2. The method of claim 1, wherein the plurality of air filled cavities comprise round cavities.

3. The method of claim 1, further comprising: embedding at least one permanent marker in the hydrogel material.

4. The method of claim 3, wherein the permanent marker comprises a metallic marker.

5. The method of claim 1, wherein the hydrogel material cured in the curing process forms a hyperechoic hydrogel material that is configured to, when inserted into tissue, gradually hydrate over time by moisture in said tissue and gradually expand and become increasingly hypoechoic as it expands and absorbs hypoechoic water.

6. The method of claim 5, further comprising: embedding a permanent marker within the hydrogel material, wherein the permanent marker is embedded within the hydrogel material that is configured to enhance the contrast between the permanent marker and said hypoechoic water to facilitate location of the permanent marker using ultrasound.

7. The method of claim 1, wherein the plurality of air filled cavities are formed to be completely encapsulated within the hydrogel material.

8. The method of claim 1, wherein the plurality of air filled cavities comprises at least one cavity having a portion in open communication with a surface of the hydrogel material.

9. The method of claim 1, wherein the plurality of air filled cavities comprises at least one cavity comprising angles.

10. The method of claim 1, wherein the plurality of air filled cavities comprises at least one cavity forming a sinusoidal shaped cavity.

11. The method of claim 1, wherein the plurality of air filled cavities comprises at least one cavity formed to have two ends each in open communication with a surface of the hydrogel material.

12. The method of claim 1, further comprising placing at least one shaped insert in the hydrogel material and removing the insert at least one shaped from the hydrogel material, and wherein the hydrogel comprises at least one cavity formed by the at least one shaped insert.

13. The method of claim 12, wherein at least one of the plurality of air filled cavities is formed to be completely encapsulated within the hydrogel material.

14. The method of claim 13, wherein at least one of the plurality of air filled cavities is formed to have a portion in open communication with a surface of the hydrogel material.

15. The method of claim 12, wherein placing the at least one shaped insert includes placing a plurality of inserts positioned in groups in the hydrogel material.

16. The method of claim 1, wherein the step of forming the body of the hydrogel marker includes forming the body including a hydrogel material configured to contain 80-90 percent water.

17. The method of claim 1, wherein the step of forming the body of the hydrogel marker includes forming the body including a hydrogel material configured to contain 80-90 percent water, further comprising the step of embedding a permanent hyperechoic marker in the center of the hydrogel material.

18. The method of claim 1, wherein the step of forming the body of the hydrogel marker includes forming the body including peg-based hydrogel material.

19. The method of claim 1, wherein the step of forming the body of the hydrogel marker includes forming the body including PGA/PLA free, peg-based hydrogel material.

20. The method of claim 1, wherein the step of forming the body of the hydrogel marker includes forming the body including a hydrogel material configured to contain water when hydrated to provide two imaging stages with imaging stage one being at initial deployment when the cured hydrogel is in a dry solid state to provide hyperechoic imaging of the hydrogel material under ultrasound and with imaging stage two being when the hydrogel is hydrated after initial deployment to provide hypoechoic imaging under ultrasound.

21. The method of claim 20, further comprising the step of embedding a permanent hyperechoic marker in the center of the hydrogel material to provide at imaging stage two a contrast to the hypoechoic hydrated hydrogel material.

* * * * *